(12) United States Patent
Hulten

(10) Patent No.: US 7,279,277 B2
(45) Date of Patent: *Oct. 9, 2007

(54) METHODS FOR CLINICAL DIAGNOSIS

(75) Inventor: Maj Anita Hulten, Birmingham (GB)

(73) Assignee: Simeg Limited, Birmingham (GB)

( * ) Notice: Subject to any disclaimer, the term of this patent is extended or adjusted under 35 U.S.C. 154(b) by 465 days.

This patent is subject to a terminal disclaimer.

(21) Appl. No.: 10/257,923

(22) PCT Filed: Apr. 20, 2001

(86) PCT No.: PCT/GB01/01767

§ 371 (c)(1),
(2), (4) Date: Feb. 21, 2003

(87) PCT Pub. No.: WO01/81626

PCT Pub. Date: Nov. 1, 2001

(65) Prior Publication Data

US 2003/0165927 A1    Sep. 4, 2003

(30) Foreign Application Priority Data

Apr. 20, 2000 (GB) ................. 0009784.0

(51) Int. Cl.
 C12Q 1/68 (2006.01)
 C12Q 1/34 (2006.01)
 C12Q 1/44 (2006.01)
 C12P 19/34 (2006.01)
 G01N 1/30 (2006.01)
 G01N 33/48 (2006.01)
 C07H 21/02 (2006.01)
 C07H 21/04 (2006.01)

(52) U.S. Cl. ............... 435/6; 435/91.1; 435/18; 435/19; 435/40.5; 435/40.51; 536/23.1; 536/23.5

(58) Field of Classification Search ............ None
See application file for complete search history.

(56) References Cited

U.S. PATENT DOCUMENTS 5,714,325 A * 2/1998 Bianchi ................ 435/6
5,834,193 A * 11/1998 Kozlowski et al. ........ 435/6
6,136,540 A * 10/2000 Tsipouras et al. ........ 435/6

FOREIGN PATENT DOCUMENTS

| EP | 0 430 402 A | 6/1991 |
| WO | 94/02646 A | 2/1994 |
| WO | 98/39474 A | 9/1998 |

OTHER PUBLICATIONS

Youngren et al, "Sychrony in telomere length of human fetus", Hum. Genet., (1988); pp. 640-643.
Iwama et al, "Telomeric length and telmoerase activity vary with age in peripheral blood cells obtained from normal individuals", Hum. Genet., (1998), pp. 397-402.
Verma et al., Lancet (1998) 352, 9-12.
Poon et al., Research Letters (2000) 356, 1819-1820.

* cited by examiner

*Primary Examiner*—Diana Johannsen
*Assistant Examiner*—Amanda Shaw
(74) *Attorney, Agent, or Firm*—Nixon & Vanderhye P.C.

(57) ABSTRACT

A method for the identification of human foetal cell nuclei is provided wherein the method involves subjecting chromosomes of cell nuclei to exonucleolytic digestion by an enzyme so as to remove end regions of each chromosome; and detecting the presence of a DNA sequence remaining in foetal DNA but absent from maternal DNA as a result of the digestion process. Once identified, the foetal DNA can be subject to diagnosis for example to detect chromosomal abnormalities.

11 Claims, 2 Drawing Sheets

Telomere differences

-Telomere length difference

-Enzymatic digestion

Dual FISH

-Telomere FISH

A

-Chromosome Y FISH

B

Dual FISH

-Telomere FISH

A

-Chromosome 21 FISH

B

METHODS FOR CLINICAL DIAGNOSIS

This application is the US national phase of international application PCT/GB01/01767 filed 20 Apr. 2001, which designated the United States of America.

The present invention relates to a method for the identification of foetal cell nuclei and the genetic material therein, such as DNA or chromosomes, in a maternal sample such as a blood or vaginal sample. Foetal genetic material identified in this way can then be used in e.g. prenatal diagnosis.

Chromosome disorders are among the most common genetic disease in humans. Constitutional chromosome disorders range in incidence from more than 50% of the lethality associated with miscarriage during the first trimester of pregnancy as well as around 5% of intrauterine or perinatal deaths. In addition 0.5% of live-born children have a constitutional chromosome abnormality.

Chromosome abnormalities may be either numerical or structural. Numerical abnormalities, implying a change from the normal diploid chromosome number of 46 in somatic tissues include trisomies (one extra chromosome), monosomies (one chromosome missing) and polyploidy (whole extra set of chromosomes). Structural rearrangements, caused by chromosome breakage followed by healing of the broken chromosome ends in aberrant positions, include so called translocations, inversions and insertions.

Structural chromosome rearrangements can occur in balanced form, in which case the genetic material remains the same as normal. Carriers of structural chromosome abnormalities are usually not showing any symptoms (unless damage has occurred of genes at the breakpoints). Structural chromosome abnormalities can also occur in unbalanced form, in which case some genetic material is deleted and/or duplicated. This will usually lead to developmental delay including live-born children with physical and mental handicaps.

The most common chromosome abnormality occurring as an entity in the human population is trisomy 21, associated with Down Syndrome. It is generally accepted that around 1/650 live-born children has trisomy 21 Down Syndrome characterised by more or less severe psychomotor development delay. There is no substantial difference in the incidence of trisomy 21 Down Syndrome in different countries world-wide.

The diagnosis of trisomy 21 Down Syndrome in child and adulthood is usually performed by chromosome analysis following in vitro culture of blood lymphocytes. The cell culture procedure takes 2-3 days to allow accumulation of enough cells in the metaphase stage of the cell cycle, when chromosomes are sufficiently condensed for their individual identification by standard chromosome banding technology.

The only clearly documented clinical risk factor for having a child with regular trisomy 21 Down Syndrome concerns maternal age. Thus it is generally accepted that there is an increasing risk for having a trisomy 21 child with advancing maternal age, which in the highest age group of more than 45 years may be over 10% of pregnancies. Screening programmes of pregnant women to identify those that are most likely to be carrying a child with trisomy 21 are in existence. These screening programmes include analysis of maternal blood samples for biochemical characteristics as well as ultrasonograhy of the foetus with the aim especially to look at the thickness of the skin of the neck, which is characteristically increased in foetuses with Down Syndrome and some other chromosome disorders.

Pregnant women over a certain age, usually 35 years, as well as women identified by screening programmes to have an increased risk, are routinely offered invasive procedures (chorionic villus sampling and/or amniocentesis) to allow foetal cell sampling for chromosome analysis. Such invasive methods, as well as being uncomfortable for the mother, are associated with an increased risk of miscarriage. There is a need therefore to provide a more efficient way of carrying out prenatal diagnosis without resorting to such invasive sampling methods.

It is well known that foetal cells may be detected in maternal blood during pregnancy, being present in the order of 1 in 10.000 to 1 in 10 million. It is also well recognised that this provides the potential for 'non-invasive' prenatal diagnosis of foetal conditions such as the most common trisomy 21 Down syndrome.

Down syndrome and some other fetal cytogenetic conditions, as well as complications in pregnancy such as pre-eclampsia and preterm labour and the post partum development of autoimmune disease, may be characterised by increased fetomaternal transfusion, leading to higher levels of fetal cells in maternal blood (reviews in Pertl and Bianchi Semin Perinatol 23, 5, 393-402, 1999; Bianchi Eur J Obstet Gynecol Reprod Biol 92, 1, 103-8,2000).

Much effort and huge resources, have been devoted to identification of foetal cells in maternal blood, using in particular immunological detection systems, followed by enumeration of chromosome number, using fluorescence in situ hybridisation (FISH) with chromosome-specific probes (review in Hahn et al. Mol Hum Repr 4, 6, 515-521, 1998, Editorial).

Samples obtained using less invasive methods from the pregnant mother will commonly contain a some maternal cells with a relatively small number of foetal cells. Current methods for foetal cell isolation include the use of antibodies, gradient fractionation, preferential maternal cell lysis, and cell sorting. However, maternal cells still tend to dominate any foetal cells recovered (see e.g. Al-Mufti et al Amer J Med Genet 85, 1, 66-75, 1999). There are still significant difficulties associated with the using these samples for non-invasive prenatal diagnosis, although the interest generated by any indications that such a technique is possible is large (see Hulten, The Lancet, 357,963-4, 2001).

It is well known that the telomeres, constituting repeated DNA sequences that cap the ends of chromosomes, vary such that young people have a higher number of the repeats than older people. It is thought that DNA replication is not taking place at the very ends of the telomere repeats. This means that, at each cell division, the telomeres, become shorter than before. It is also thought that this shortening eventually leads to cell death (review in De Lange, Science 279, 334-335, 1998).

Telomeres of all human chromosomes contain the same DNA core repeat. The variation in telomere length with age of the individual is a general phenomenon observed on all the chromosomes. Depending upon the age of the individual, variation in repeat length of telomeres is estimated to be in the order of 2-30 Kb of DNA.

Chromosome-specific telomere lengths can be measured using special software and microscopy image analysis of chromosomes hybridised with telomeric probes (Poon et al Cytometry 36, 267-278, 1999). These investigations indicate that there may be some variation between individual cell nuclei in the telomere content of individual chromosomes. Nevertheless, as already mentioned, there is a substantial decrease in telomere length with the age of the subject. On this basis, the telomere length of individual chromosomes in foetal cells should be longer than in the new-born child, and longer still than in the adult (see De Pauw et al Cytometry 32, 3, 163-1690). It is implicit therefore that foetal cells have longer telomeres, i.e. a higher copy number per chromosomes of the telomere DNA repeats, than cells from the mother (Friedrich et al Pediatr Res 49, 2, 256-6, 2001).

The applicants have found that this characteristic can be used as a basis for differentiation between maternal and foetal cell nuclei and/or the genetic material therein, in particular chromosomes and DNA, present in a maternal tissue sample such as a blood or serum sample.

Thus according to the present invention there is provided a method for the identification of foetal cell nuclei, chromosomes and DNA in a maternal blood (including the serum or plasma components) or vaginal sample, said method comprising (a) subjecting chromosomes of cell nuclei in said sample to exonucleolytic digestion by an enzyme so as to remove end regions of each chromosome, and (b) detecting the presence of DNA sequences remaining in foetal cell nuclei but absent from maternal cell nuclei as a result of said digestion process.

In effect, the invention uses differences in the number of telomere repeats in foetal and maternal DNA as a basis for direct identification of foetal cell nuclei in maternal tissue samples. During step (a) DNA of chromosomes in the cell nuclei are digested from the end region inwards. Telomeric segments of all chromosomes present in the sample are digested first during this process. Exonucleolytic digestion is carried out for a period of time sufficient to eliminate at least all maternal telomeric DNA sequences.

If digestion is halted at this point, foetal chromosomes will retain some telomeric DNA. This DNA can then be detected using for example, a labelled probe specific for the telomere DNA which will in this situation hybridise only to foetal DNA.

Preferably, the method is carried out using a maternal blood sample including the serum and/or plasma components. The expression "blood sample" as used herein encompasses whole blood, serum or plasma from which nucleated cells have been isolated by standard techniques.

The method may be effected in situ in the cells. In this case, exonucleolytic enzyme is introduced into the cell nuclei through the nuclear membranes. These may be permeabilized for the purpose, for example using an enzyme such as lysolecithin, saponin or Triton X 100 to perforate the nuclear membranes.

In a preliminary step, chromosomes from the cells are fixed for analysis by standard techniques using fixatives such as Carnoy (Acetic Acid:Methanol 3:1) or Formaldehyde.

Where the sequence detected in step (b) is a chromosome marker, it may be preferable that it is a near telomeric (subtelomeric or telomeric) chromosome marker, as this gives rise to the possibility that the marker can itself be useful in prenatal diagnosis. In any event, the identification of foetal cell nuclei, containing chromosomes and DNA, can be used as a preliminary step to 'non-invasive' prenatal diagnosis.

In a particularly preferred embodiment, DNA present in the sample after digestion is hybridised with a first labelled probe specific for the said DNA sequences, such as the telomere sequences. Most preferably, the said first probe is labelled with a visible label in particular a fluorescent label, and fluorescence from the sample is detected. This may be effected in situ, for example on a cell slide, or alternatively, a flow sort method could be used to separate foetal cell nuclei (which have become fluorescently labelled) from maternal cell nuclei.

Suitable enzymes for conducting exonucleolytic digestion include BAL31. It may be preferable to use enzyme which digest specific regions of the DNA only, in order to ensure a more controllable digestion process. In particular, digestion is effected in a three step process, in which, in a first step, 3' extension DNA is removed, in a second step, 3'-5' ss regions are excised and in a third step, ss regions are digested. Suitable enzymes for effecting the first and third steps include Mungbean nuclease, and for the second step, suitable enzymes include Exonuclease III.

The conditions, such as enzyme concentrations, buffer systems, temperature and time of incubation, required in order to provide reliable digestion to allow differentiation between maternal and foetal cell nuclei, containing chromosomes and DNA, require careful selection and depend upon factors such as the particular enzyme being used.

As a result of the variation in the numbers of telomeric DNA sequence repeats between different chromosome ends, it is desirable first to "calibrate" the enzyme system, preferably in a chromosome specific manner. Calibration of this type may be effected by analysing the results of exonucleolytic telomeric digestion of chromosomes under various conditions.

Another means of calibrating particular enzyme systems is to obtain base-line information on the telomeric length of each individual chromosome end in maternal and foetal tissue samples. This may be done using fluorescence in situ hybridisation (FISH) of telomeric DNA sequences at the metaphase stage of the cell cycle. The individual telomeres at each chromosome end may be highlighted using FISH with telomeres in combination with subtelomeric DNA probes. Measurements of telomeric sequences may be performed by Microscopy Image Analysis, using a Comparative Genomic Hybridisation (CGH) software programme.

Blood samples from foetuses subject to cordocentesis and cord blood samples, obtained at delivery, can also be utilised, with a view to obtaining additional base-line information on the normal variation in length of telomeric DNA sequences for each chromosome arm in maternal and foetal tissue samples. Once identified using the method of the invention, foetal DNA, chromosomes or cell nuclei may be subject to pre-natal diagnosis, for example to determine the presence of chromosome/DNA aberrations such as Down syndrome, Edward Syndrome or Klinefelter Syndrome or other information such as the sex of the foetus.

In addition, the information obtainable using the method of the invention, in particular relating the amount of concentration of foetal cells in the maternal sample, may be useful in prenatal screening/diagnosis as well as in diagnosis of a range of maternal conditions. These include complications in pregnancy such as pre-eclampsia, in predicting the risk of pre-term labour, and in the later development of autoimmune disease.

A particular method by which prenatal diagnosis of chromosome aberrations can be achieved is by contacting the sample with a second labelled probe which is specific for a particular chromosome or diagnostic region of DNA under conditions in which the probe hydridises to DNA within the sample. Detection of this second probe in nuclei, chromosomes or DNA already identified as being of foetal origin will therefore provide information about the foetus. Depending upon the particular diagnostic purpose, it may be useful if the second probe is specific for chromosome 18, 21 or 13, and/or the X or Y chromosomes.

It would be expected that a combination of FISH probes for X/Y, 13, 18 and 21 detects about 70% of all abnormalities, which are currently identified by full chromosome analysis (karyotyping) of amniotic fluid samples in unselected pregancies. Excluding high risk pregnancies (ascertained by e.g. family history with either parent being a known carrier of a structural chromosome abnormality such as a translocation, or foetal structural abnormality has bee detected by ultrasound) then the detection rate is increased to over 99%. It should also be noted that probes, specific for different types of abnormalities may be used.

Preferably the said second probe carries a visible label such as a fluorescent label. In a particularly preferred embodiment of the method of the invention, in step (b) the foetal DNA sequence is detected using a first fluorescently labelled probe and the second probe carries a fluorescent label which fluoresces at a wavelength which is different to that of said first probe, wherein foetal DNA is detected by detecting fluorescence from said first label. Once identified, the wavelength of the detected fluorescence is changed to that of the second probe, to see whether fluorescence from both probes emanates from similar cell nuclei, chromosomes or DNA. This can be achieved easily, for example by changing filters on the fluorescence detector employed.

In a preferred option the subtelomeric markers in question should be located as distal as possible among the chromosome-unique DNA sequences within each chromosome arm. These markers will be preselected for each chromosome end separately with respect to locations. Suitably the DNA markers selected are strategically localised in subtelomeric chromosome positions, containing chromosome-specific unique DNA. This location is preferred for one main reason.

The use of subtelomeric or telomeric chromosome/DNA markers will allow quantification of not only numerical chromosome aberrations (such as trisomies) but also some relatively common unbalanced structural chromosome rearrangements such as unbalanced translocations. An unbalanced translocation will be identified as a duplication for one chromosome-specific subtelomeric or telomeric marker in combination with a deletion for another chromosome-specific subtelomeric or telomeric marker, dependent on which chromosomes are involved in the translocation. In addition, other relatively common chromosome aberrations should be identifiable this or similar ways. These include extra marker chromosomes such as foetal iso 12 p, iso 18 p, or isodic 15, associated with foetal malformations and/or psychomotor developmental delay, and which would give rise to 4 extra markers in relation to the normal situation.

By appropriate selection of fluorescent DNA markers used in the prenatal foetal diagnosis, the majority of chromosome abnormalities, leading to foetal development disturbance may be determined using this method. These include Down Syndrome, Klinefelter Syndrome and Edward Syndrome as illustrated hereinafter.

In one embodiment of the invention, a maternal tissue sample such as a blood sample (including the plasma or serum components) is taken and nucleated cells, which are not dividing cells, are isolated therefrom using conventional methods, for example by Lymphoprep (Sigma) or a Percoll (Amersham Pharmacia) method.

The membranes of cell nuclei are then permeabilised using standard techniques, for example exposure to the chemical agents lysolecithin, saponin or Triton X100.

In a following step the chromosomes of cell nuclei are fixed by conventional techniques such as exposure to Carnoy fixative (Acetic Acid:Methanol, 3:1) or Formaldehyde.

The cell nuclei are then spread on a microscopy slide and incubated with an exonucleolytic enzyme such as BAL 31, for a period of time, which is sufficient to digest maternal telomeres, but leave some foetal telomeric DNA.

A pan-telomeric labelled probe such as a fluorescently labelled probe is applied to the cells. The probe will adhere to the telomeric segments of the chromosomes in the foetal cell nuclei but will not interact with chromosomes of maternal cell nuclei, which have lost their telomeric segments.

If examined on a slide at this point, foetal cell nuclei will fluoresce whilst maternal cell nuclei do not. Alternatively, fluorescent foetal cells can be separated from maternal cells using flow cytometry methods as are known in the art.

In a particular embodiment, secondary, differently labelled probes are introduced into the cells after separation. Suitably the differently labelled probes also carry a visible label such as a different fluorescent label (fluorophore). Whether or not the DNA from the foetal cell has bound to the second probe can be determined using fluorescence microscopy and separate filters, as is well known in the art.

Fluorophore commonly used include DAPI, fluorescein, FITC, Cy3, Cy5, rhodamine dyes and Texas Red.

According to a further aspect of the invention, there is provided a kit for identifying foetal cell nuclei, chromosomes and DNA in a maternal blood or vaginal sample, said kit comprising an exonucleolytic enzyme, capable of digesting terminal regions of DNA, and a labelled probe, such as a fluorescently labelled probe, for detecting specific DNA sequences found in terminal regions of chromosomes.

The kit may contain one or more further reagents or commodities, which are required for effecting the method as described above. In particular, the kit may further comprise a second labelled probe, such as different fluorescently labelled probes, which are specific for certain DNA sequences of specific chromosome segments, therefore allowing diagnosis of different chromosome conditions.

The kit may also contain an agent for isolation of nuclear cells (such as Percoll or Lymphoprep) and/or an agent for perforation of nuclear membranes (such as lysolecitin, saponin or Triton X 100) and/or an exonucleolytic enzyme (such as BAL 31) for digestion of telomeres.

It is important to note that the independent identification of foetal cell nuclei per se is obligatory for reliable non-invasive prenatal diagnosis (Hulten, The Lancet, 357, 963-4, 2001). The invention provides a means for achieving this.

It should, on the other hand, also be noted that a variety of combinations of fluorophores (directly or indirectly labelled) may be used for different FISH colour signals for the identification of telomere sequences and chromosome specific sequences, as is well known in the art. FISH per se is currently a rapidly developing field.

Finally it is important to recognise that the FISH-FISH procedure is in itself simple and rapid, in particular in comparison to alternative techniques, as described by other investigators. The total hands-on time for enrichment and making preparations, including in situ hybridisation, is around 6 hours. Some steps will lend themselves to application of automation. This is also true for the microscopy analysis, where automated fluorescence spot counting is already in existence in house, using commercially available computer software.

BRIEF DESCRIPTION OF THE DRAWINGS

The invention will now be particularly described by way of example with reference to the accompanying diagrammatic drawings in which.

EXAMPLE 1

Figure 1:
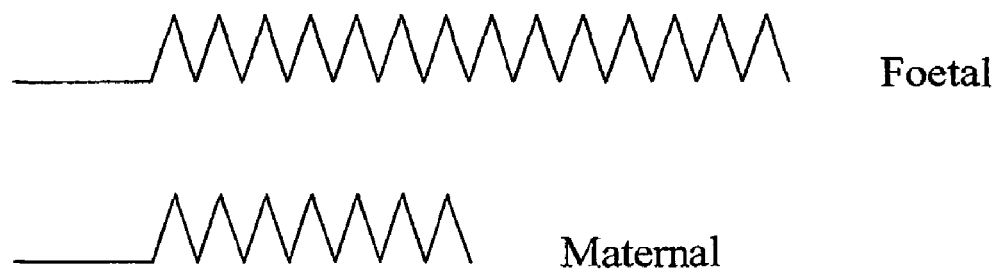
FIG. 1 illustrates schematically telomere differences found in maternal and foetal chromosomes/DNA, and the effects of enzymatic digestion thereon.
Figure 1:
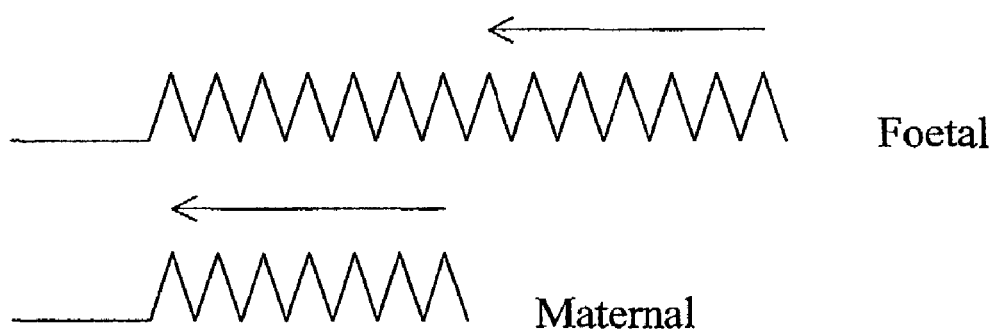

Nucleated cells were isolated from adult female blood samples, and from amniotic fluid samples (containing foetal nucleated cells). The two cell types were mixed in suspension containing varying proportions of foetal and adult cells ranging from 1/10, and 1/100 to 1/1000 vol %.

Thereafter suspensions were exposed to lysolecithin to induce permeabilisation of cellular/nuclear membranes, followed by fixation and preparation of microscopy slides and exposure to exonucleolytic DNA digestion. These cells were then hybridised with pan-telomeric probes and subsequently with chromosome-specific probes for fluorescence microscopy analysis.

1) Cell Preparation 10 mls of fresh blood in EDTA tubes were mixed with 10 mls of Phosphate Buffer Saline (PBS). Then 10 mls of Lymphoprep (Nycomed Pharma AS, Oslo, Norway) was placed into a 50 ml tube and 10 mls of the diluted blood slowly layered on top.

The tubes were centrifuged at 2000 rpm for 30 minutes. The thin layer of lymphocytes just below the plasma was then removed by tilting the tube and aspirating out the layer of cells (3-5 mls), using a fine pipette. Thereafter the separated lymphocytes were diluted with PBS to make the final volume up to 20 mls. These cells were then centrifuged at 2000 rpm for 15 minutes. The supernatant was discarded and the cell pellet was dissolved in 5 mls of PBS.

Amniotic fluid samples from male trisomy 21 pregnancies were centrifuged at 2000 rpm for 15 minutes. The supernatant was carefully discarded and the cell pellet resuspended in 5 mls of PBS.

2) Cellular Mixtures

Varying mixtures of adult female cells and male foetal cell samples were prepared to make up a final solution of 10 mls. The proportions of foetal to adult cells varied from 1/10, 1/100 and 1/1000 vol %.

3) Permeabilisation of Cellular/Nuclear Membranes

Lysolecithin (5 μg/ml in sodium acetate) was added to the mixtures of lymphocytes and amniotic fluid samples. These cells were incubated at 4° C. for 2 minutes. The reaction was stopped by adding 2.5 mls of paraformaldehyde. The cells were then spun at 2000 rpm for 15 minutes and washed twice in PBS containing 1% Bovine Serum Albumin (BSA).

4) Slide Preparation and Fixation

200 μl of cell suspension were placed onto a clean slide and left to dry. Cells were then fixed with 200 μl of 2% formaldehyde added onto the slide and left for 10 minutes. The slides were then washed in PBS and dehydrated through an ethanol series.

5) Exonucleolytic Enzyme Digestion

Slides were aged on a hotplate (40°-50° C.) for 2 hours. Enzyme digestion was carried out with 1-5 units of Bal 31 enzyme (New England Bio labs) in 50 μl of buffer per slide. Slides were placed on a 37° C. hotplate for 10 minutes. Enzymatic reaction was stopped by washing the slides in 2×SSC at room temperature. Slides were then dehydrated through an ethanol series and air-dried.

6) PNA FISH for the Telomeres

The slides were washed in Tris-Buffered Saline (TBS), 3.7% Formaldehyde and pre-treatment solution, according to the manufacturer's recommendations for use of the pan-telomeric PNA kit (Dako, Glostrup, Denmark). Slides were then dehydrated through an ethanol series and air-dried. 10 μl of FITC labelled probe was added to each slide and covered with a glass coverslip. Slides were incubated at 80° C. for 3 minutes and then at room temperature in the dark for 30 minutes. The slides were put through rinse and wash solutions and dehydrated through an ethanol series. After air drying the slides, they were counterstained with Vectashield (Vector Laboratories, Peterborough, UK), containing DAPI, and covered and sealed with coverslips.

7) Hybridisation with Probes Specific for Chromosomes 21, 13, 18, X and Y Using Vysis Aneuploidy Detection Kit The coverslips were removed from the slides by immersing them in acetone for 2 minutes. The slides were then dehydrated and air-dried. Two hybridisation areas were marked on the slides using a diamond tipped scribe. Target DNA was denatured by immersing in 70% formamide: 30% 2×SSC at 73° C. for 5 minutes. 10 μl of CEP 18/X/Y probe mix was applied to target area 1 and 10 μl of LSI 13/21 probe mix (Vysis, US) was applied to the target area 2 and a coverslip placed over the probe solution. Coverslips were sealed using rubber cement and slides placed in a pre-warmed humidified container in a 37° C. incubator for 16 hours or overnight. Coverslips were removed and slides washed in 0.4×SSC/0.3% NP-40 solution at 73° C. for 2 minutes. Slides were then placed in 2×SSC/0.1% NP-40 solution at room temperature for 1 minute. When completely dried 10 μl of DAPI II counterstain (Vysis, US) was applied to the target area and sealed under a coverslip.

8) Microscopy

Slides were screened using a Zeiss axioplan epifluorescence microscope with ×100 objective. Signals were viewed using appropriate filters and images acquired using a CCD camera with SmartCapture software (Vysis, US). Slides were scanned starting in the upper left corner of the coverslip and moving from top to bottom.

Analysis was initially performed with respect to telomere fluorescence using FITC filter. The positions of positive and negative cells were recorded using an England Finder (Graticules Ltd, Kent, UK). Cell nuclei were thereafter re-examined on area 1 and 2 using the Orange filter (Vysis, US) for identification and enumeration of chromosomes Y, and 21, respectively.

9) Results

Figure 2:
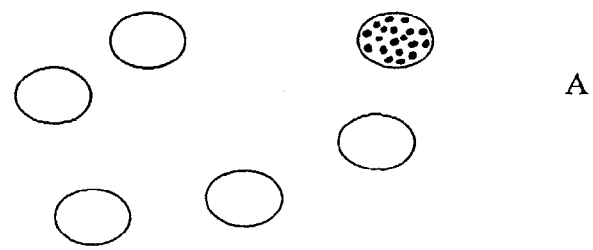
FIG. 2 illustrates schematically, the results of analysis using the method of the invention of a mixed population of maternal and foetal cells using (a) a telomere specific FISH probe, and (b) a chromosome Y specific FISH probe.
Figure 2:
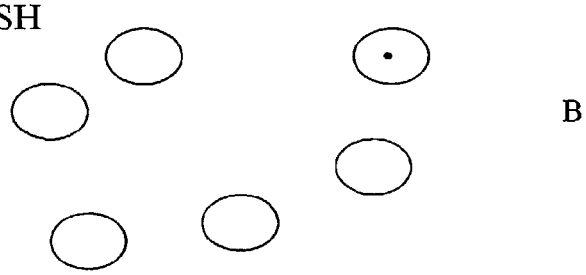
Figure 3:
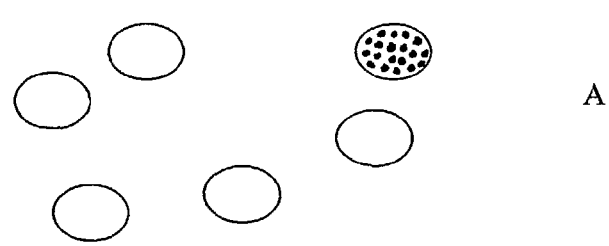
FIG. 3 illustrates schematically, the results of analysis using the method of the invention of a mixed population of maternal and foetal cells using (a) a telomere specific FISH probe, and (b) a chromosome 21 specific FISH probe.
Figure 3:
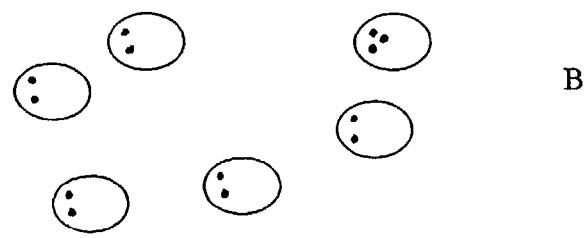

Fluorescence microscopy using the FITC filter showed telomeric signals in some cell nuclei, while signals were absent or nearly absent from other nuclei. The proportion of nuclei showing these telomeric signals corresponded to those expected from the mixtures of foetal and adult cell nuclei prepared and analysed. Thus the lower the concentration of foetal cells, the higher the proportion of non-fluorescent nuclei, and vice-versa. Images were captured of suitable populations of cell nuclei, and their positions recorded. (FIGS. 2A and 3A).

Subsequently the same cell populations were analysed using the Orange filter (Vysis, US) for identification of foetal male trisomy 21 nuclei, expected to carry a Y chromosome and three chromosome 21 signals. A total of 1000 nuclei per cellular mix category (1/10, 1/100, 1/1000 vol % foetal to adult cells) were analysed for the Y signal in area 1 of the slide, the chromosome 21 signal in the area 2 of the slide.

A 97.3% correspondence between nuclei having telomeric fluorescence, and therefore being interpreted as foetal, and the occurrence of a Y signal was found. This result on Y fluorescence is compatible with that found by the corresponding analysis of pure foetal cell populations, being 95-100%, according to the manufacturer's manual. (FIG. 2B).

A slightly lower correspondence between nuclei having telomeric fluorescence, and therefore being interpreted as foetal, and the occurrence of three chromosome 21 signals, was seen. This varied between 83-90% in repeated experiments. Yet again these results correspond to those we routinely record in amniotic fluid samples in case of foetal trisomy, and is within the range recorded in the manufacturer's manual. (FIG. 3B).

10) Interpretation

These results demonstrate that it is possible to discriminate between foetal and adult cells, using a dual FISH analysis of telomeres and chromosome-specific probes, following enzymatic digestion of telomeres in a timecourse.

EXAMPLE 2

Prenatal Diagnosis of Foetal 47,XY+21 Down Syndrome from Maternal Blood

1. Pregnancy and Blood Sample 12 ml of blood is drawn into 2 edetic acid (EDTA) tubes by venipuncture from a pregnant woman at 16 weeks gestational age, following written informed consent with Ethical Approval from the Local Ethical Committee.

[It should be noticed that in this and the following examples have used a relatively small amount of blood. Larger samples of maternal blood should allow collection of a larger population of foetal cells, and may therefore be preferable.]

2. Enrichment of Foetal Cells

Enrichment of foetal nucleated cells in plasma from the maternal blood is performed using a Triple Density Gradient according to the protocol as described (Ganshirt et al., Diagnostic Cytogenetics, Springer Lab Manual, 1999 R. -D. Wagner, Fetal Cells in Maternal blood, pp 401-415) with slight modifications.

12 ml of the EDTA blood is added to 12 ml of Phosphate Buffer Solution (PBS) and mixed by inverting the tube. 6 ml of the blood/PBS mixture is pipetted into four 15 ml polystyrol tubes. Three layers of Percoll$^R$ (Amersham Pharmacia) are underlayered, using a long and thin canula attached to a syringe. Initially 3 ml of 40% Percoll is underlayered, followed by 3 ml of 45% and 3 ml of 50% Percoll. The suspension is then centrifuged at 500 g for 30 min. The plasma layer is removed and transferred to a clean tube and again centrifuged at 500 g for 10 min. The cell pellet is washed in PBS and fixed with 3:1 methanol:acetic acid according to standard technique routinely used for cytogenetic preparations.

3. Slide Preparation and Fixation

The fixed cell suspension is placed on a silanised microscopy slide and left to dry. The cell suspension is further formaldehyde fixed in a coplin jar for 10-min (50 ml PBS, 0.5 g $MgCl_2$, 1.3 ml of formaldehyde, dehydrated through an ethanol series (70%, 95%, 100%) and air-dried.

4. Exonucleolytic Enzyme Digestion

Enzyme digestion is carried out with 3 units of Bal 31 enzyme following the protocol as described in Example 1 (paragraph 5).

5. FISH Using Pantelomere, Y and 21 Probe Combination 0.5 µl of All Telomere Digoxygenin labelled Probe (Appligene Oncor), 1 µl of LSI Chromosome 21 spectrum orange probe (Vysis Ltd.) and 1 µl of CEP (III) spectrum aqua probe (Vysis Ltd) are mixed together with 7.5 µl of Hybrisol VI (Oncor Appligene) for each slide. 10 µl of this probe mix is placed on the microscopic slide containing the target cells. The slide is then denatured on a hotplate at 75° C. for 5 min, sealed with rubber solution and hybridised overnight at 37° C. in a humidified chamber.

Post hybridisation washes are carried out the next day. Slides are washed in 50% formamide at 43° C. for 15 min, in 2×SSC at 37° C. for 8 min, and then in 1×PBT at room temperature. 30 µl of fluorescein labelled anti-digoxigenin antibody is placed on the slide and kept at 37° C. for 5 min. Finally, the slide is washed in 1×PBT three times for 2 min, air dried and counterstained with DAPI.

6. Microscopy Analysis

The slide is screened using a Zeiss axioplan epifluorescence microscope with a ×40 objective. Signals are viewed using appropriate filters, and images acquired using a CCD camera with SmartCapture image acquisition and analysis system (Vysis/Applied Imaging) and relevant images stored.

A total of 1000 cell nuclei are examined. The majority, i.e. 995/1000 (99.5%) do not contain the telomeric (green) signal, and these are interpreted to be of maternal origin. Images are captured of the remaining 5 nuclei using the FITC, spectrum orange and spectrum aqua filters. These 5/1000 nuclei may contain both green telomeric signals and an aqua Y signal, and are therefore interpreted to be of male foetal origin. However, where these 5 nuclei also contain three red signals, this is indicative that the foetus may have the karyotype 47,XY+21 predictive of Down syndrome.

SUMMARY AND CONCLUSION

Following enrichment of foetal cells in the plasma compartment by a Percoll gradient, FISH investigations are applied, using the probe cocktail Tel/Y/21 for identification of the presence of telomeric sequences as well as the enumeration of Y and chromosome 21 signals.

This example illustrates that it will be possible to identify the chromosome constitution with respect to the probe cocktail applied, Y/21 in cell nuclei that are diagnosed as being of foetal origin per se by virtue of their remaining telomere fluorescence after in vitro enzymatic depletion. This combination will allow conclusions to be drawn as to whether the foetus is male and has trisomy 21 Down syndrome.

EXAMPLE 3

Prenatal Diagnosis of Foetal 47,XX,+21 Down Syndrome from Maternal Blood

1. Pregnancy and Blood Sample 12 ml of blood is drawn into 2 edetic acid (EDTA) tubes by venipuncture from a pregnant woman at 16 weeks gestational age, following written informed consent with Ethical Approval from the Local Ethical Committee.

2. Enrichment of Foetal Cells

Enrichment of foetal nucleated cells in plasma from the maternal blood is performed using a Triple Density Gradient according to the protocol as described (Ganshirt et al., Diagnostic Cytogenetics, Springer Lab Manual, 1999 R. -D. Wagner, Fetal Cells in Maternal blood, pp 401-415) with slight modifications.

12 ml of the EDTA blood is added to 12 ml of Phosphate Buffer Solution (PBS) and mixed by inverting the tube. 6 ml of the blood/PBS mixture is pipetted into four 15 ml polystyrol tubes. Three layers of Percoll$^R$ (Amersham Pharmacia) are underlayered, using a long and thin canula attached to a syringe. Initially 3 ml of 40% Percoll is underlayered, followed by 3 ml of 45% and 3 ml of 50% Percoll. The suspension is then centrifuged at 500 g for 30 min. The plasma layer is removed and transferred to a clean tube and again centrifuged at 500 g for 10 min. The cell pellet is washed in PBS and fixed with 3:1 methanol:acetic acid according to standard technique routinely used for cytogenetic preparations.

3. Slide Preparation and Fixation

The fixed cell suspension is placed on a silanised microscopy slide and left to dry. The cell suspension is further formaldehyde fixed in a coplin jar for 10-min (50 mls PBS, 0.5 g MgCl$_2$, 1.3 ml of formaldehyde), dehydrated through an ethanol series (70%, 95%, 100%) and air-dried.

4. Exonucleolytic Enzyme Digestion

Enzyme digestion is carried out with 3 units of Bal 31 enzyme following the protocol as described in Example 1 (paragraph 5).

5. FISH Using Pantelomere, X/Y, 13, 18 and 21 Probe Combination 0.5 µl of All Telomere Digoxygenin labelled Probe (Appligene Oncor) is mixed with 0.5 µl of Biotin labelled StarFISH Human Chromosome Pantelomeric Probe (Cambio). The telomere mix is then added to 10 µl of MultiVysion™ PGT (Vysis Ltd). This probe mix is placed on the microscopic slide containing the target cells. The slide is then denatured on a hotplate at 75° C. for 5 min, sealed with rubber solution and hybridised overnight at 37° C. in a humidified chamber.

Post hybridisation washes are carried out the next day. Slides are washed in 50% formamide at 43° C. for 15 min, in 2×SSC at 37° C. for 8 min, and then in 1×PBT at room temperature. 30 µl of the premixed Dual Colour Detection Reagent (Oncor Appligene) is placed on the slide and kept at 37° C. for 5 min. Finally, the slide is washed in 1×PBT three times for 2 min, air dried and counterstained with DAPI.

6. Microscopy Analysis

The slide is screened using a Zeiss axioplan epifluorescence microscope with ×40 objective. Signals are viewed using appropriate filters, and images acquired using a CCD camera with SmartCapture image acquisition and analysis system (Vysis/Applied Imaging) and relevant images stored.

A total of 1000 cell nuclei are examined. The majority, i.e. 995/1000 (99.5%) do not contain the telomeric (yellow) signal and these are preliminary interpreted to be of maternal origin. Images are captured of the remaining 5 nuclei using the FITC, spectrum Orange, spectrum Aqua and spectrum Gold filters. These 5/1000 nuclei contain yellow telomeric signals and are therefore interpreted to be of foetal origin.

These nuclei may, for example, also have two red signals for chromosome 13, two green signals for chromosome 21, two aqua signals for chromosome X, and three blue signal corresponding to chromosome 18, but no gold signal for the Y chromosome. Such a pattern would indicate that the foetus has the karyotype 47,XX+18, predictive of Edward syndrome.

SUMMARY AND CONCLUSION

Following enrichment of foetal cells in the plasma compartment by a Percoll gradient, FISH investigations are applied, using the probe cocktail Tel/13/18/X/Y/21 for identification of the presence of telomeric sequences as well as the enumeration of 13, 18, X, Y and chromosome 21 signals.

This example illustrates that it will be possible to identify the chromosome constitution (with respect to the probe cocktail 13/18/X/Y/21) in cell nuclei that are diagnosed as being of foetal origin per se by virtue of their remaining telomere fluorescence after in vitro enzymatic depletion. This combination will allow conclusions to be drawn as to whether the foetus is female and has Edward syndrome.

EXAMPLE 4

Prenatal Diagnosis of Foetal 47, XXY Klinefelter Syndrome from Maternal Blood 1. Pregnancy and Blood Sample 12 ml of blood was drawn into 2 edetic acid (EDTA) tubes by venipuncture from a pregnant woman at 16 weeks gestational age, following written informed consent with Ethical Approval from the Local Ethical Committee.

2. Enrichment of Foetal Cells

Enrichment of foetal nucleated cells in plasma from the maternal blood was performed using a Triple Density Gradient according to the protocol as described (Ganshirt et al., Diagnostic Cytogenetics, Springer Lab Manual, 1999 R. -D. Wagner, Fetal Cells in Maternal blood, pp 401-415) with slight modifications.

12 ml of the EDTA blood is added to 12 ml of Phosphate Buffer Solution (PBS) and mixed by inverting the tube. 6 ml of the blood/PBS mixture is pippetted into four 15 ml polystyrol tubes. Three layers of Percoll$^R$ (Amersham Pharmacia) are underlayered, using a long and thin canula attached to a syringe. Initially 3 ml of 40% Percoll is underlayered, followed by 3 ml of 45% and 3 ml of 50% Percoll. The suspension is then centrifuged at 500 g for 30 min. The plasma layer is removed and transferred to a clean tube and again centrifuged at 500 g for 10 min. The cell pellet is washed in PBS and fixed with 3:1 methanol:acetic acid according to standard technique routinely used for cytogenetic preparations.

3. Slide Preparation and Postfixation

The fixed cell suspension is placed on a silanised microscopy slide and left to dry. The cell suspension is further formaldehyde fixed in a coplin jar for 10-min (50 mls PBS, 0.5 g $MgCl_2$, 1.3 ml of formaldehyde), dehydrated through an ethanol series (70%, 95%, 100%) and air-dried.

4. Exonucleolytic Enzyme Digestion

Enzyme digestion was carried out with 3 units of Bal 31 enzyme following the protocol as described in Example 1 (paragraph 5).

5. FISH Labelling Using Pan Tel and 18/X/Y Probe Combination 9.5 µl of Aneuvysion CEP 18/X/Y (Vysis Ltd) and 0.5 µl of All Telomere Digoxygenin labelled Probe (Oncor) are placed on the slide and a coverslip applied. The slide is then denatured on a hotplate at 75° C. for 5 min, sealed with rubber solution and hybridised overnight at 37° C. in a humidified chamber.

Post hybrididsation washes are carried out the next day. Slides are washed in 50% formamide at 43° C. for 15 min, in 2×SSC at 37° C. for 8 min, and then in 1×PBT at room temperature. 30 µl of fluorescein labelled anti-digoxigenin antibody is placed on the slide and kept at 37° C. for 5 min. Finally, the slide is washed in 1×PBT three times for 2 min, airdried and counterstained with a drop of 4',6-diamino-2-phenylindole (DAPI, Vectashield Ltd).

6. Microscopy Analysis

The slide is screened using a Zeiss axioplan epifluorescence microscope with a ×40 objective. Signals are viewed using appropriate filters, and images acquired using a CCD camera with SmartCapture image acquisition and analysis system (Vysis/Applied Imaging) and relevant images stored.

A total of 1000 cell nuclei are examined. The majority, i.e. 995/1000 (99.5%) do not contain the telomeric (green) signal and these are interpreted to be of maternal origin. On the other hand, 5 nuclei contain telomere signals as well as a Y signal, and these are interpreted to be of foetal origin.

In 4 of these 5 nuclei there may be two X signals, a combination of signals which is compatible with the foetal karyotype 47,XXY, predictive of Klinefelter syndrome. The remaining cell may have one X and one Y signal, as expected in a normal 46,XY male. All 5 cells may have two signals for chromosome 18.

In such a case, it is possible to conclude that the foetus has the karyotype 47,XXY, compatible with Klinefelter syndrome. It should be noted however, that it is not possible to differentiate between the possibility that the occurrence of a single cell nucleus with the XY chromosome constitution represents a technical artefact with failure of X hybridisation (a false negative foetal cell) or the alternative that the foetus is in fact a Klinefelter mosaic with the karyotype 46,XY[1]/47,XXY[4].

SUMMARY AND CONCLUSION

Following enrichment of foetal cells in the plasma compartment by a Percoll gradient, we can perform FISH investigations, using the probe coctail X/Y/18 (Vysis Ltd) for enumeration of X, Y and chromosome 18, and the All Telomere Digoxygenin-labelled Probe (Appligene Oncor) for identification of telomere sequences.

This example illustrates that it is possible to identify the foetal chromosome constitution with respect to the probe cocktail X/Y/18 in cell nuclei, which are diagnosed as being of foetal origin by virtue of their remaining telomere fluorescence after in vitro enzymatic depletion, using the pan-telomeric probe. Based on the concordance between cell nuclei with XXY and XY and telomere fluorescence, we may conclude that the foetus has Klinefelter Syndrome in either non-mosaic or mosaic form.

The invention claimed is:

1. A method for the identification of human foetal cell nuclei, containing chromosomes, in a human maternal blood sample, said method comprising (a) obtaining cell nuclei from a human maternal blood sample by using a density gradient to achieve enrichment for fetal nucleated cells; (b) treating the cell nuclei obtained in (a) with an agent that makes the cell nuclei permeable; (c) fixing the chromosomes of said cell nuclei; (d) subjecting the chromosomes to exonucleolytic digestion by an enzyme to remove end regions of each chromosome, and (e) identifying foetal cell nuclei based upon the presence of telomere sequences that are remaining in the foetal cell nuclei but absent from maternal cell nuclei as a result of removing end regions of each chromosome.

2. A method according to claim 1 wherein said agent that makes the cell nuclei permeable is selected from the group consisting of lysolecithin, saponin and octylphenol ethoxylate.

3. A method according to claim 1 wherein in (c), the chromosomes of said cell nuclei are fixed by exposure to Carnoy (Acetic Acid:Methanol, 3:1) or formaldehyde.

4. A method according to claim 1 wherein said telomere sequences remaining in the foetal cell nuclei are detected using a primary labeled probe which is specific for said telomere sequences.

5. A method according to claim 4 wherein said primary labeled probe has a fluorescent label.

6. A method according to claim 1 wherein the telomere sequences remaining in the foetal cell nuclei are identified using a fluorescence in-situ hybridization assay (FISH).

7. A method according to claim 1 wherein the enzyme is BAL31.

8. A method according to claim 1 wherein the exonucleolytic digestion is accomplished in stages in which, in a first step, 3' extension DNA is removed, in a second step, 3'-5' single stranded regions are excised and in a third step, single stranded regions are digested.

9. A method according to claim 8 wherein the first step is accomplished using Mungbean nuclease.

10. A method according to claim 8 wherein the second step is accomplished using Exonuclease III.

11. A method according to claim 8 wherein the third step is accomplished using Mungbean nuclease.

* * * * *